(12) United States Patent
Zadoyan et al.

(10) Patent No.: US 8,231,612 B2
(45) Date of Patent: Jul. 31, 2012

(54) METHOD OF MAKING SUB-SURFACE PHOTOALTERATIONS IN A MATERIAL

(75) Inventors: Ruben Zadoyan, Irvine, CA (US); Michael Karavitis, Huntington Beach, CA (US); Ronald M. Kurtz, Irvine, CA (US)

(73) Assignee: AMO Development LLC., Santa Ana, CA (US)

( * ) Notice: Subject to any disclaimer, the term of this patent is extended or adjusted under 35 U.S.C. 154(b) by 1289 days.

(21) Appl. No.: 11/942,627

(22) Filed: Nov. 19, 2007

(65) Prior Publication Data

US 2009/0126870 A1   May 21, 2009

(51) Int. Cl.
*A61B 18/20* (2006.01)
(52) U.S. Cl. .............................................. 606/5; 606/11
(58) Field of Classification Search ................... 264/400, 264/482; 606/5, 10, 11, 12; 219/121.62, 219/121.68, 121.69, 121.83, 121.85
See application file for complete search history.

(56) References Cited

U.S. PATENT DOCUMENTS

| | | | |
|---|---|---|---|
| 4,764,930 A | 8/1988 | Bille et al. | |
| 4,901,718 A | 2/1990 | Billie et al. | |
| 4,907,586 A * | 3/1990 | Bille et al. | 606/5 |
| 5,520,679 A | 5/1996 | Lin | |
| 5,599,340 A | 2/1997 | Simon et al. | |
| 5,656,186 A * | 8/1997 | Mourou et al. | 219/121.69 |
| 5,800,424 A | 9/1998 | Sumiya | |
| 5,993,438 A | 11/1999 | Juhasz et al. | |
| 6,110,166 A | 8/2000 | Juhasz | |
| 6,325,792 B1 | 12/2001 | Swinger et al. | |
| RE37,585 E | 3/2002 | Mourou et al. | |
| 6,451,006 B1 | 9/2002 | Billie | |
| 6,610,050 B2 * | 8/2003 | Bille | 606/5 |
| 6,641,577 B2 | 11/2003 | Billie | |
| 7,131,968 B2 | 11/2006 | Bendett et al. | |
| 2001/0010003 A1 | 7/2001 | Lai | |
| 2001/0016736 A1 | 8/2001 | Lin | |
| 2001/0037105 A1 | 11/2001 | Lin | |

(Continued)

FOREIGN PATENT DOCUMENTS

DE   102005039833 A1   3/2007

(Continued)

OTHER PUBLICATIONS

Heisterkamp A., et al., "[Optimizing laser parameters for intrastromal incision with ultra-short laser pulses]" "Opimierung der Laserparameter Fuer Die Intrastromale Schnittfuehrung Mittels Ultrakurzer Laserpulse", Ophthalmologe, Sprnger, Berlin, DE, vol. 98, No. 7, Jul. 1, 2001, pp. 623-628, XP002368976, ISSN: 0941-293X.

*Primary Examiner* — Geoffrey S Evans
(74) *Attorney, Agent, or Firm* — AMO Development LLC.

(57) ABSTRACT

A method of photoaltering a material using a pulsed laser beam includes selecting a first pulse energy and a first focal point separation based on a relationship of pulse energy and focal point separation combinations enabling layer separation of the material by photoalteration, and scanning the pulsed laser beam along a scan region at the first pulse energy and the first focal point separation. The relationship has a slope and has a distinct change in the slope. The distinct change in the slope is associated with a second pulse energy of the relationships and the first pulse energy is equal to or less than second pulse energy.

17 Claims, 5 Drawing Sheets

U.S. PATENT DOCUMENTS

| | | |
|---|---|---|
| 2002/0111607 A1* | 8/2002 | Bille .................................. 606/5 |
| 2003/0132208 A1 | 7/2003 | Cutler |
| 2003/0208189 A1 | 11/2003 | Payman |
| 2003/0212387 A1 | 11/2003 | Kurtz et al. |
| 2003/0229339 A1* | 12/2003 | Bille .................................. 606/5 |
| 2004/0199150 A1 | 10/2004 | Lai |
| 2004/0209410 A1 | 10/2004 | Tanaka |
| 2004/0243112 A1 | 12/2004 | Bendett et al. |
| 2005/0245915 A1 | 11/2005 | Loesel et al. |
| 2006/0027544 A1 | 2/2006 | Pailthorp et al. |
| 2006/0095024 A1* | 5/2006 | D'Ippolito ........................ 606/5 |
| 2006/0155265 A1 | 7/2006 | Juhasz et al. |
| 2006/0195076 A1 | 8/2006 | Blumenkranz et al. |
| 2007/0055221 A1* | 3/2007 | Lubatschowski et al. ........ 606/5 |
| 2007/0078447 A1* | 4/2007 | Weinacht et al. ................. 606/5 |
| 2007/0088409 A1 | 4/2007 | Bischoff et al. |
| 2007/0179479 A1 | 8/2007 | Bille |
| 2007/0235543 A1 | 10/2007 | Zadoyan et al. |
| 2008/0051769 A1* | 2/2008 | Mrochen et al. .................. 606/4 |
| 2009/0118716 A1 | 5/2009 | Brownell |
| 2009/0118718 A1 | 5/2009 | Raksi et al. |
| 2009/0126870 A1 | 5/2009 | Zadoyan et al. |

FOREIGN PATENT DOCUMENTS

| | | |
|---|---|---|
| EP | 1473006 | 11/2004 |
| EP | 1591087 | 11/2005 |
| EP | 1731120 | 12/2006 |
| EP | 1834615 | 9/2007 |
| WO | 9717903 | 5/1997 |
| WO | 2004/003625 | 1/2004 |
| WO | 2004/017878 | 3/2004 |
| WO | 2005/058216 | 6/2005 |

* cited by examiner

METHOD OF MAKING SUB-SURFACE PHOTOALTERATIONS IN A MATERIAL

BACKGROUND OF THE INVENTION

1. Field of the Invention

The field of the present invention is generally related to modifying a material through photoalteration and more particularly, to systems and methods of making sub-surface photoalterations in the material.

2. Background

Pulsed laser beams include bursts or pulses of light, as implied by name, and have been used for photoalteration of materials, both inorganic and organic alike. Typically, a pulsed laser beam is focused onto a desired area of the material to photoalter the material in this area and, in some instances, the associated peripheral area. Examples of photoalteration of the material include, but are not necessarily limited to, chemical and physical alterations, chemical and physical breakdown, disintegration, ablation, vaporization, or the like.

Applying pulsed laser photoalteration near, but not at, the surface of a material (e.g., sub-surface) can be challenging. For example, photoalteration can be utilized to produce an incision in the material. The minimum cutting depth, i.e., the distance of the incision from the surface of the material, associated with current methods of photoalteration is generally based on the type of material and the energy of the laser pulse applied to the material. For incisions that are attempted closer to the surface than the minimum cutting depth for a given material and pulse energy, the photoalteration of the material may generate gases which in turn may rupture the surface of the material. Although decreasing the energy of the laser pulses may minimize or eliminate surface rupture associated with these gases, many other factors minimize or eliminate surface rupture associated with these gases, many other factors affect the photoalteration process and may be considered for optimization. Such factors include pulse width, energy distribution within the pulse, scan pattern, and scan rate, among other factors.

Accordingly, it is desirable to provide a system and method for sub-surface photoalteration of a material that optimizes photoalteration for the particular material. It is also desirable to provide a system and method for sub-surface photoalteration of a material that can create thin flaps while minimizing or eliminating surface rupture by gases that may be associated with the photoalteration. Additionally, other desirable features and characteristics of the present invention will become apparent from the subsequent detailed description and the appended claims, taken in conjunction with the accompanying drawings and the foregoing technical field and background.

SUMMARY OF THE INVENTION

The present invention is directed towards photoaltering a material using a pulsed laser beam. In one embodiment, a method of photoaltering a material in a scan region using a pulsed laser beam is provided. The method includes, but is not necessarily limited to, selecting a first pulse energy and a first focal point separation based on a relationship of pulse energy and focal point separation combinations enabling layer separation of the material by photoalteration, and scanning the pulsed laser beam along the scan region at the first pulse energy and the first focal point separation. The relationship has a slope and a distinct change in the slope, and the distinct change in the slope is associated with a second pulse energy on the relationship. The first pulse energy is equal to or less than the second pulse energy.

In another embodiment, a method of separating a surface layer from a material via photoalteration is provided. The method includes, but is not necessarily limited to, determining a relationship for the material based on laser pulse energies enabling layer separation of the material through photoalteration as a function of laser pulse focal point separations within the material, identifying a target pulse energy value from the relationship corresponding to a distinct change of the slope, generating a beam of laser pulses, and scanning the beam of laser pulses along a region within the material with an operating focal point separation corresponding with the target pulse energy value. The relationship has a slope. Each of the laser pulses has an energy less than or equal to the target pulse energy value. The region underlies the surface layer.

In yet another embodiment, a system for sub-surface photoalteration of a material is provided including a laser configured to produce a pulsed laser beam having a first pulse energy and a first focal point separation, and a controller coupled to the laser. The controller is configured to determine the first pulse energy and the first focal point separation based on a relationship of pulse energy and focal point separation combinations enabling layer separation of the material by photoalteration. The relationship has a slope and a distinct change in the slope, and the distinct change in the slope is associated with a second pulse energy on the relationship. The first pulse energy is equal to or less than the second pulse energy.

BRIEF DESCRIPTION OF THE DRAWINGS

In the drawings, wherein like reference numerals refer to similar components.

DETAILED DESCRIPTION

Figure 1:
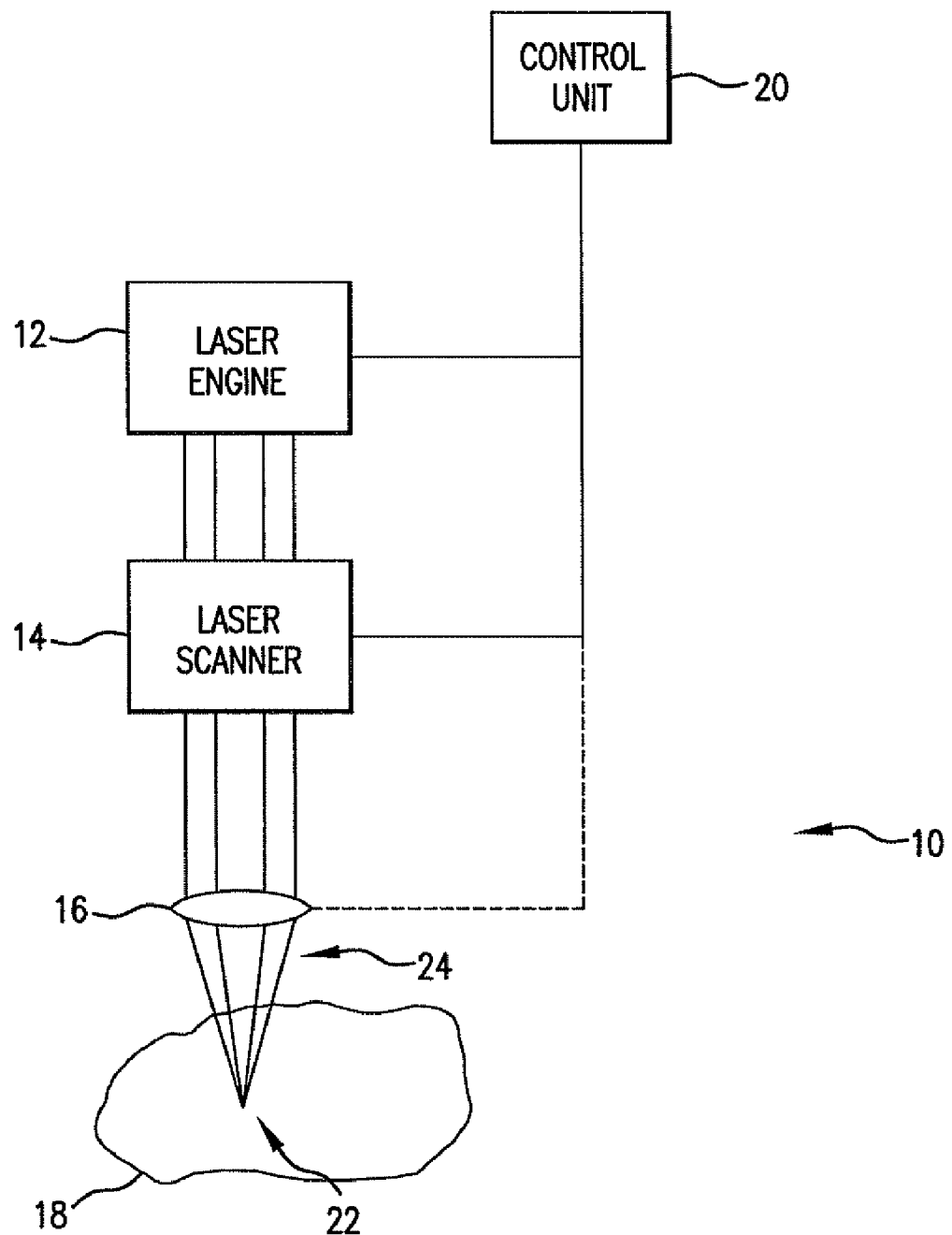
FIG. 1 is a block diagram of a system for photoaltering a material in accordance with one embodiment of the present invention.

The present invention provides systems and methods for sub-surface photoalterations in a material. Photoalteration of materials may be accomplished using a pulsed laser beam. To provide the pulsed laser beam, chirped pulse laser amplification systems may be used, such as described in U.S. Pat. No. RE37,585, describing methods of optimizing pulse energy and pulse width, for a given material, for photoalteration. U.S. Patent Publication No. 2004/0243111 also describes similar methods of photoalteration. Other devices or systems may also be used to generate the pulsed laser beam.

In general, for a particular material (e.g., organic, inorganic, or a combination thereof) and pulsed laser beam, a relationship of pulse energy versus focal point separation is pre-determined (e.g., prior to the actual photoalteration of the material for a desired effect, such as producing an incision). In one embodiment, for a particular material and a pulsed laser beam (e.g., having a pre-determined wavelength and/or pulse shape), a relationship of pulse energy versus focal point separation is determined. The pulse energy is the energy associated with each laser pulse of the pulsed laser beam for layer separation in the material through photoalteration. The focal point separation is the spatial separation between focal points of laser pulses of the pulsed laser beam when the pulsed laser beam is directed into the material. This relationship exhibits a distinct change in slope (e.g., a change greater than about ten degrees (10°)) between a first substantially linear relationship and a second substantially linear relationship) as both the focal point separation and the pulse energy decrease. Although systems for photoaltering material may vary to some degree (e.g., using different lasers or the like), this distinct change is generally consistent for a given material and pulsed laser beam (e.g., having a given wavelength and/or pulse shape). With this relationship identified, the pulsed laser beam is scanned along a scan region within the material. This scanned laser beam has an operating pulse energy and an operating focal point separation based upon this relationship. In one embodiment, the operating pulse energy of the scanned laser beam is selected to be equal to or less than the pulse energy associated with the distinct change in slope.

With these operating values, the material may be photoaltered in the scan region to produce a sub-surface incision with acceptable layer separation of the material and with minimal pulse energy, in one embodiment. Additionally, an operating depth of the focal point (e.g., of at least one laser pulse) of the pulsed laser beam may be selected. The operating depth is the minimum sub-surface depth at which the focal point of the pulsed laser beam is proximally located with respect to the surface of the material without gas rupture of the surface of the material. This value may also be pre-determined (e.g., prior to the actual photoalteration of the material for the desired effect, such as producing the sub-surface incision) using the operating pulse energy and operating focal point separation.

Referring to the drawings, a system 10 for photoaltering a material 18 (e.g., producing an incision in the material) is shown in FIG. 1 in accordance with one embodiment of the present invention. In addition to photoaltering the material 18, the system 10 may be used for identifying or pre-determining the relationship of pulse energy and focal point separation for the material 18 and determining the minimum sub-surface depth (i.e., for the focal point of the pulsed laser beam). The system 10 includes, but is not necessarily limited to, a laser engine 12 producing a pulsed laser beam 24, a laser scanner 14 positioning the pulsed laser beam 24 in a plane perpendicular to the axis (not shown) of the pulsed laser beam 24, focusing optics 16 controlling a focal point 22 of the pulsed laser beam 24, and a control unit 20 coupled to the laser engine 12 and the laser scanner 14. The control unit 29 may optionally be coupled to the focusing optics 16 for automated control thereof, for example. To produce the pulsed laser beam 24 with the desired operating characteristics for the particularly material 18, the control unit 20 can modify the settings of the laser engine 12 and the laser scanner 14.

Data points may be empirically determined from different pulse energies as a function of focal point separations. For example, for different focal point separations, the laser engine 12 outputs pulsed laser beams at different pulse energies, and the pulse energy and focal point separation combinations that produce layer separation within the material 18 are recorded as data points. The control unit 20 can store these data points and determine the relationship of pulse energy and focal point separation for a particular material, such as by generating a curve to fit the data points (e.g., a best-fit curve), although other methods may be used. In one embodiment, these curves can be stored (e.g., as a look-up table in a memory of the control unit 20 or the like) for selective recall and application on an identical or similar material using an identical or similar pulsed laser beam. In another embodiment, the curves may also be periodically recalibrated (e.g., by empirically re-determining the data points). Although these data points may vary for a given system (e.g., having a laser engine operating at a particular wavelength or), the curves generated to fit the corresponding data points are substantially similar in shape.

From this relationship of pulse energy and focal point separation, the control unit 20 can select the operating pulse energy and the operating focal point separation for the pulsed laser beam 24 to create separable layers within the material 18. Additionally, data points may be empirically determined from different sub-surface depths (i.e., of the focal point of the pulsed laser beam) as a function of focal point separations. For example, for different combinations of pulse energy and focal point separation (e.g., based on the relationship of pulse energy and focal point separation), the laser engine 12 outputs pulsed laser beams at different sub-surface depths, and the sub-surface depths that lack surface rupture of the material are recorded as data points. The control unit 20 can also store these sub-surface depths as data points.

Once the operating pulse energy and operating focal point separation are selected from the relationship of pulse energy versus focal point separation, the focal point 22 of the pulsed laser beam 24 may be positioned at a target area of the material 18 and scanned along a scan region. In this embodiment, the target area is a sub-surface area. The focal point 22 of the pulsed laser beam 24 may also be positioned at the minimum sub-surface depth corresponding with the operating pulse energy and operating focal point separation and scanned along the scan region. For ophthalmic applications, such as incising corneal flaps, the data points may be determined using a material exhibiting substantially similar physical characteristics and behavior as corneal tissue (e.g., in response to photoalteration), thus allowing for a determination of the best-fit curve and selection of the operating pulse energy, operating focal point separation, and minimum sub-surface depth for corneal tissue without actually photoaltering corneal tissue. Recalibrations of such data points and curves may similarly be conducted on a material exhibiting substantially similar physical characteristics and behavior as corneal tissue.

Figure 2:
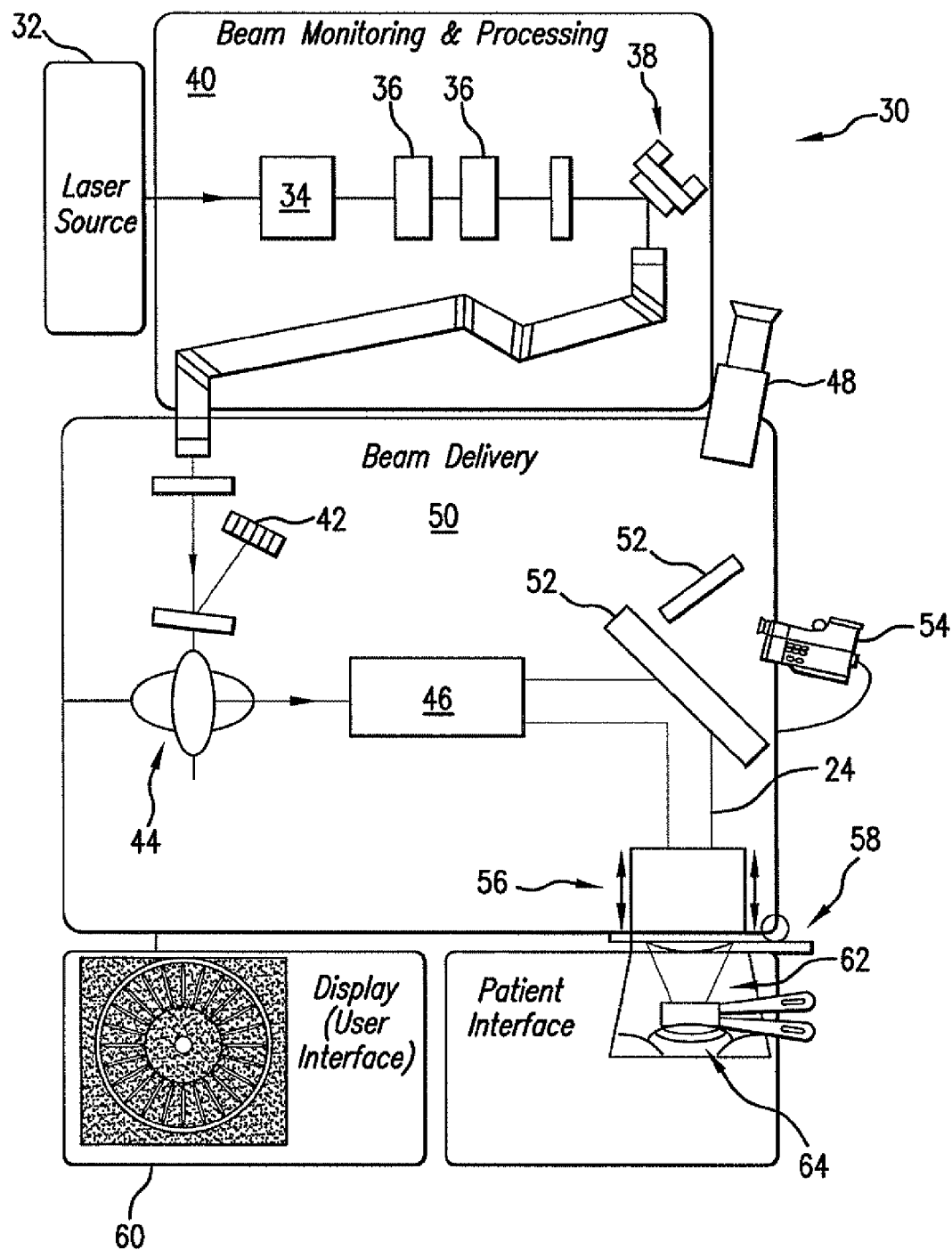
FIG. 2 is a block diagram of an ophthalmic laser system in accordance with another embodiment of the present invention.

FIG. 2 is a block diagram of an ophthalmic laser system 30 in accordance with another embodiment of the present invention. In this embodiment, the operating pulse energy and operating focal point separation, and optionally the minimum sub-surface depth, may be determined by using the ophthalmic laser system 30 and utilized to photoalter a material (i.e., the tissue of a human eye). The ophthalmic laser system 30 includes, but is not necessarily limited to, a laser source 32 providing a pulsed laser beam, a beam monitoring and processing module 40, a beam delivery module 50, and a user interface 60. The pulsed laser beam is supplied to the beam monitoring and processing module 40 where the pulse energy, the focal point separation, and optionally the minimum sub-surface depth of the pulsed laser beam are controlled. The beam delivery module 50 scans the pulsed laser beam along a desired scan region. In this embodiment, the ophthalmic laser system 30 can be coupled to an eye 64 via a patient interface 62, and the patient interface 62 may be coupled to the ophthalmic laser system 30 at a loading deck 58, for example. A display is provided by the user interface 60 for viewing the eye 64 undergoing laser treatment.

After the relationship of pulse energy and focal point separation has been identified for a particular material, in this case the eye 64, the operating pulse energy and operating focal point separation are selected by the beam monitoring and processing module 40. In one embodiment, the beam monitoring and processing module 40 includes, but is not necessarily limited to, an energy attenuator 34, one or more energy monitors 36, and an active beam positioning mirror 38. The pulsed laser beam is directed from the laser source 32 to the energy attenuator 34, then to the energy monitor 36, and then to the active beam positioning mirror 38. The active beam positioning mirror 38 directs the pulsed laser beam from the beam monitoring and processing module 40 to the beam delivery module 50. Using the energy attenuator 34 and energy monitor 36, the pulse energy of the pulsed laser beam may be varied to desired values. Additionally, the spatial separation of the focal points of the pulsed laser beam may be varied by the beam monitoring and processing module 40.

After selection of the operating pulse energy and the operating focal point, the beam delivery module 50 scans the pulsed laser beam at the desired scan region (e.g., a sub-surface region of the eye 64, such as within the corneal epithelium and on or within Bowman's layer, the stroma, Descemet's membrane, the endothelium, or the like). In one embodiment, the beam delivery module 50 includes, but is not necessarily limited to, a beam position monitor 42, an x-y scanner 44, a beam expander 46, one or more beam splitters 52, and a z-scanning objective 56. In this embodiment, the beam delivery module 50 additionally includes an operating microscope 48 and a video camera 54 to enhance viewing of the eye 64.

The pulsed laser beam is received from the beam monitoring and processing module 40 by the x-y scanner 44 and directed to the beam expander 46, and the beam expander 46 directs the pulsed laser beam to the z-scanning objective via the beam splitter(s) 52. The z-scanning objective 56 can vary the focal point depth of the pulsed laser beam. For example, the z-scanning objective 56 can vary the focal point depth to the minimum focal point depth determined for the particular material (e.g., the eye 64 or a specific region of the eye 64) and for the selected operating pulse energy and operating focal point separation.

The configuration of the ophthalmic laser system 30 may vary as well as the organization of the various components and sub-components of the ophthalmic laser system 30. For example, some sub-components of the beam delivery module 50 may be incorporated with the beam monitoring and processing module 40 and vice versa.

Figure 3:
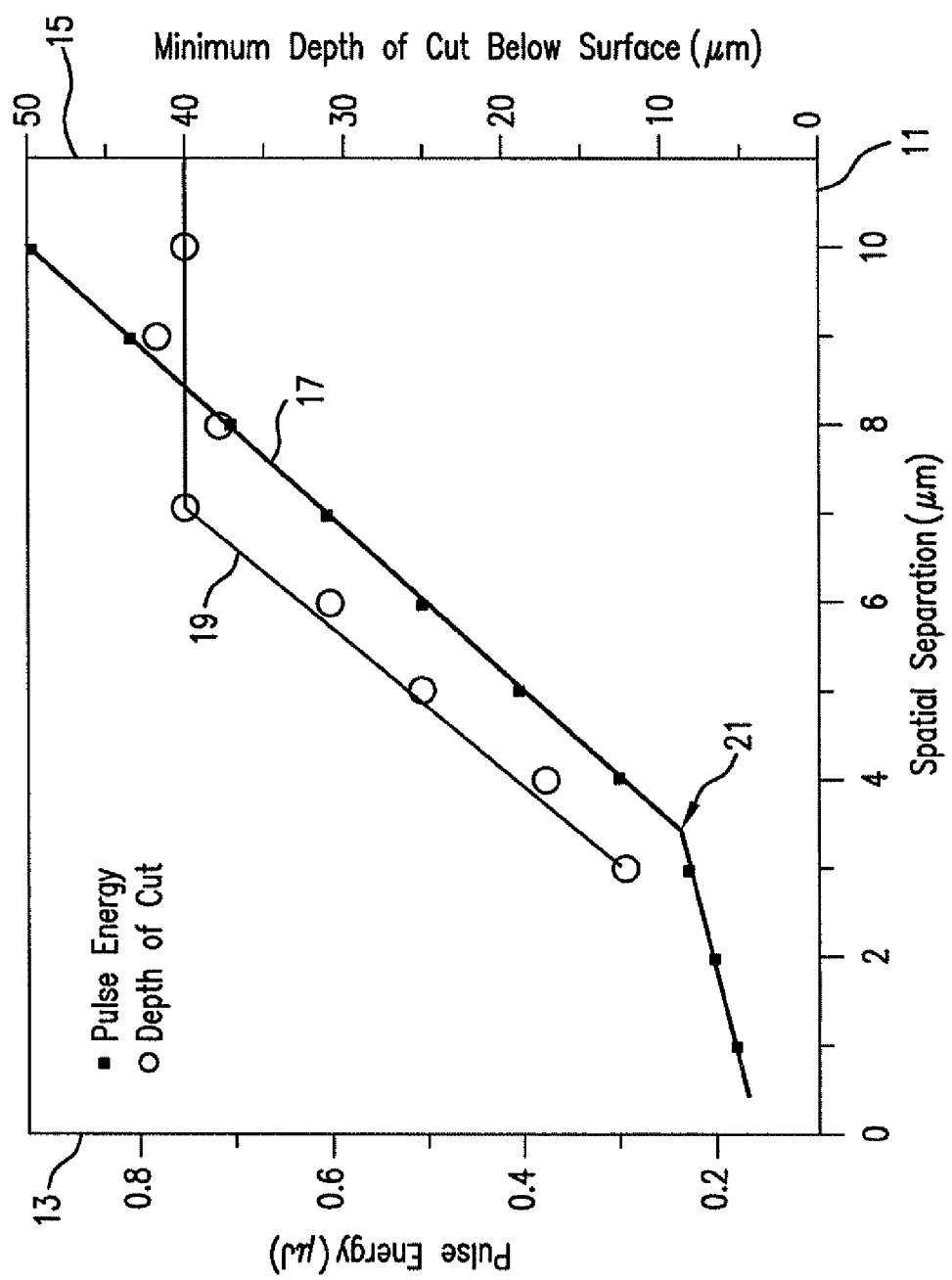
FIG. 3 is a graph illustrating a relationship between pulse energy, focal point spatial separation, and an associated minimum sub-surface depth, for a pulsed laser beam in accordance with one embodiment.

FIG. 3 is a graph of pulse energy as a function of focal point separation and minimum sub-surface depth as a function of focal point separation in accordance with one embodiment. An x-axis 11 sets forth the focal point separation, a left-hand y-axis 13 sets forth the pulse energy, and a right-hand y-axis 15 sets forth the minimum sub-surface depth. In this embodiment, a pulsed laser beam having ultra-short pulses, preferably in the femtosecond range, is directed into a selected material. The laser producing this beam may be of the type described in U.S. Pat. No. 4,764,930, producing an ultra-short pulsed beam (e.g., less than about one picosecond), such as described in one or both of U.S. Pat. Nos 5,984,916 and RE37,585. U.S. Pat. No. 5,993,438 also discloses an intrastromal photodisruption technique for reshaping the cornea using a non-UV, ultrashort (e.g., femtosecond pulse duration), pulsed laser beam that propagates through corneal tissue and is focused at a point below the surface of the cornea to photodisrupt stromal tissue at the focal point. The disclosures of the aforementioned patents are incorporated herein by reference in their entirety. Preferably, the laser is capable of generating pulses in a range of about 30 MHz to about 1 GHz, and each of these pulses has a pulse energy of less than about 800 nJ. In another embodiment, the laser may generate pulses greater than or less than this frequency range or have pulse energies greater than this energy level.

In general, data points are empirically determined by directing the pulsed laser beam into the selected material. Although variances in the data may exist based upon the particular laser equipment and the type of material used, the data is generally consistent for a selected material and a selected pulsed laser beam (e.g., operating with a known wavelength, a known pulse shape, or the like). The material may be of any type, inorganic or organic, that is susceptible to the photoalteration process. Those skilled in the art of photoalteration in any one of the various industries that employ the process will appreciate the wide range of materials to which this process may be applied. Although the graph shown in FIG. 3 illustrates relationships for one material, additional relationships may be determined, stored, and recalled for different materials. Additionally, these relationships may be correlated for materials having similar physical characteristics or behavior (e.g., in response to photoalteration).

In one embodiment, two curves 17 and 19 are generated to fit the empirically determined data points and emphasize particular features of the data points and the relationships between pulse energy, focal point separation, and minimum sub-surface depth of the focal point. For example, a pulse energy curve 17 is generated from one set of empirically determined data points, and a focal point depth curve 19 is generated from another set of empirically determined data points. The pulse energy curve 17 represents a relationship between focal point separation and pulse energy, and the focal point depth curve 19 represents a relationship between focal point separation and minimum sub-surface depth. The focal point separation is based on the minimum separation between focal points (i.e., for adjacent focal points) of the pulsed laser beam, whether consecutively or non-consecutively scanned. In practice, curves generated to fit the data points may have more subtle features than those shown in the curves 17 and 19 but are likely to display characteristics that are similar to the general characteristics associated with the curves 17 and 19, respectively.

Figure 4:
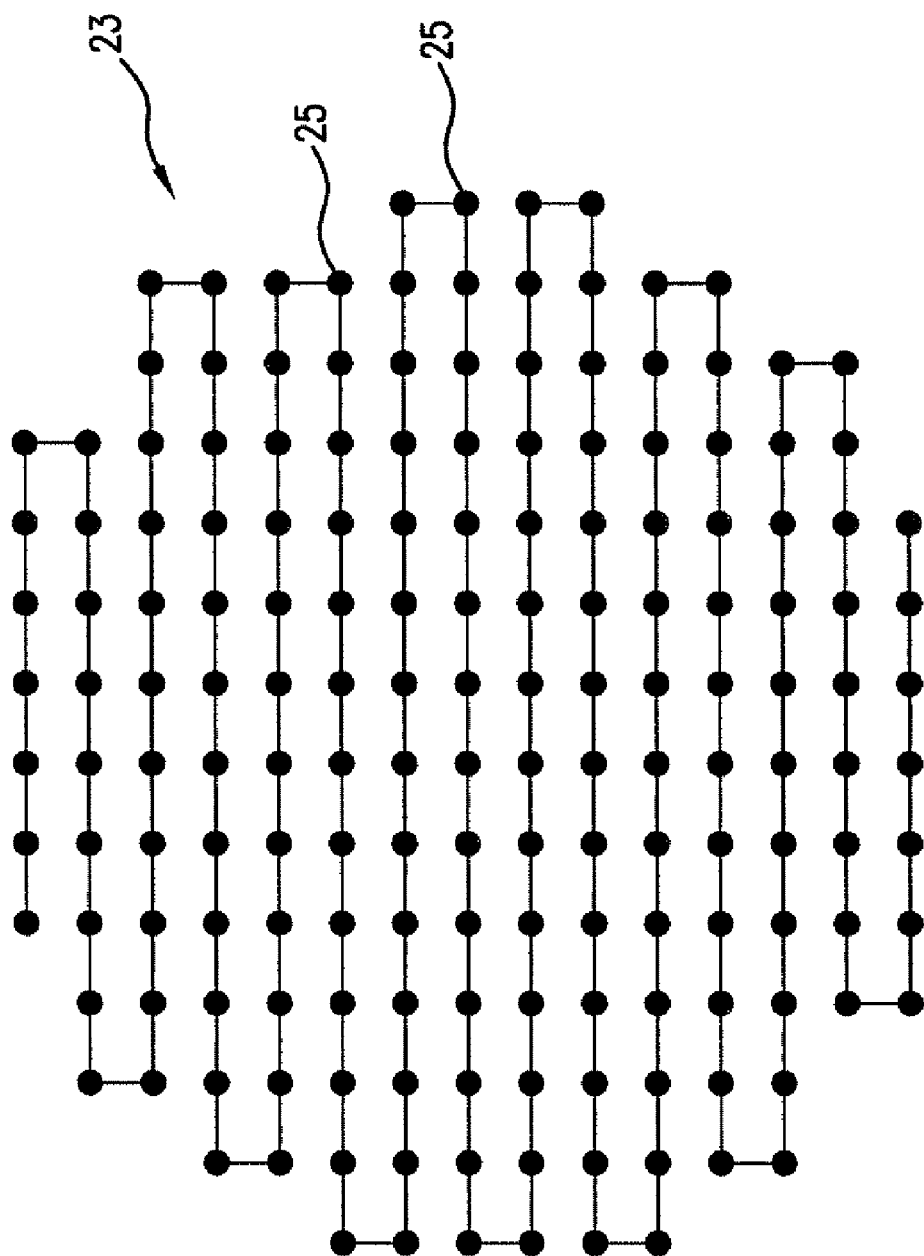
FIG. 4 is a raster scan pattern of a pulsed laser beam in accordance with one embodiment.

Generally, the data points are empirically determined by scanning the pulsed laser beam in a pre-determined raster scan pattern. FIG. 4 is a raster scan pattern 23 in accordance with one embodiment and illustrates the placement of focal points 25 of the pulsed laser beam along the raster scan pattern 23. This raster scan pattern 23 is capable of providing consistent focal point separation between consecutively scanned focal points and between adjacent focal points that lie on adjacent scan lines. A similar raster scan pattern was used to derive the data points shown in FIG. 3, although a variety of other scan patterns (e.g., more or less complex scan patterns, or the like) could also be used.

For a material, one set of data points is empirically determined based on focal point separation and pulse energy combinations that create a separable layer within the material. For example, a first pulse energy and a first focal point separation are chosen together such that, when applied to the material in a selected pattern to cover a scan region, the resulting photoalteration divides the material into separable layers. The pulse energy for layer separation, given a specific focal point separation, varies based upon the physical properties of the material. Further, the layer separation quality, i.e., how easily one layer (i.e., resulting from the photoalteration) is separable from the other layer, may be varied and typically depends upon the type of material. For example, at a selected focal point separation, higher pulse energies may be used if a relatively clean layer separation of the material is desired. On the other hand, at the same selected focal point separation, lower pulse energies may be used if partial connectivity of the layers is acceptable (e.g., requiring at least some minor mechanical separation, such as tearing, of the layers). Similar degrees of layer separation quality may be achieved by maintaining the pulse energy at a constant level and increasing or decreasing the focal point separation. For purposes of the empirical process, a pulse energy value is selected that corresponds to the minimal pulse energy achieving layer separation for a given focal point separation. In other embodiments, greater pulse energies may be used. This process is repeated for a range of focal point separations.

Referring back to FIG. 3, pulse energies are empirically tested from about 1 µm through about 10 µm of focal point separation at 1 µm intervals to determine the minimal pulse energy at which acceptable layer separation could be achieved. The pulse energy curve 17 has a distinct change in slope 21 for focal point separations between about 3 µm and about 4 µm. Through experimentation for this embodiment, an optimum separation of a relatively thin surface layer of the material is obtainable using a pulse energy and focal point separation combination based on the pulse energy curve 17 for the material. To affect a desired photoalteration, the operating pulse energy of the pulsed laser beam is preferably selected to be substantially equal to or less than the pulse energy at this distinct change in slope 21. The degree of thinness associated with the surface layer of the material is dependant upon several factors, including the physical properties of the material, the type of laser used, the energy of the laser pulses, and the selected scan pattern.

The pulsed laser beam may also be employed to empirically determine a minimum focal point depth to affect the desired photoalteration. The minimum focal point depth is the sub-surface depth within the material at which the pulsed laser beam may be focused without causing the surface of the material to rupture (i.e., due to the breakthrough of gases that may result from photoalteration of the material). In one embodiment, the process of empirically determining the data points for the focal point depth curve 19 is based on an incremental process. For example, the focal point depth of the pulsed laser beam is incrementally decreased toward the surface of the material (e.g., from a greater depth to a shallower depth within the material). Multiple laser pulses are preferably directed at each focal point depth to provide multiple data points for each focal point depth.

Figure 5:
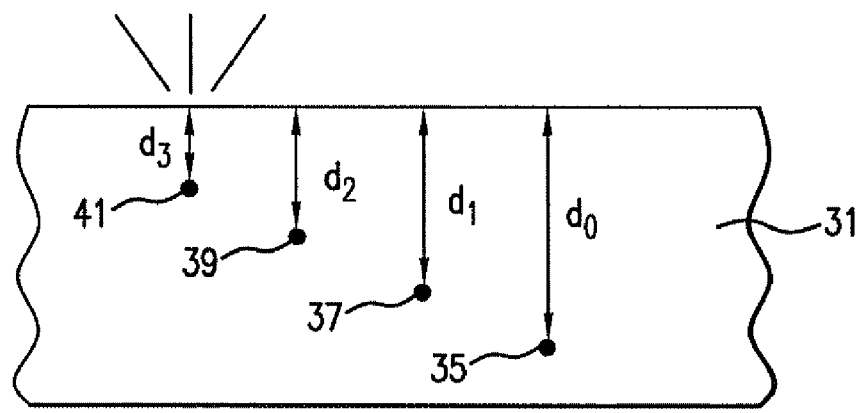
FIG. 5 is a sectional view of a material illustrating focal point depths in accordance with one embodiment.

FIG. 5 is a sectional view of a material 31 illustrating focal point depths 35, 37, 39, 41 in accordance with one embodiment. The incremental process, using multiple focal point depths within the material 31, is simplified in this embodiment. Each focal point depth 35, 37, 39, 41 is based on a single laser pulse, although multiple laser pulses may be applied at one or more of the focal point depths 35, 37, 39, 41. A first laser pulse is directed to a focal point located at a sub-surface depth at which the photoalteration process does not cause the surface to rupture (e.g., based on prior knowledge). Subsequent laser pulses are directed to additional focal points, each having a shallower sub-surface depth in comparison to the previous focal point. In one embodiment, this process continues until photoalteration by at least one of the laser pulses causes the surface to rupture thereby indicating that the minimum focal point depth has been exceeded.

The pulsed laser beam is first directed to three focal points 35, 37, 39 at sub-surface depths of $d_0$, $d_1$, and $d_2$, respectively, within the material 31, where $d_0 > d_1 > d_2$. The photoalteration centered around each of these focal points 35, 37, and 39 does not cause the surface to rupture. The fourth focal point 41 is at a sub-surface depth of $d_3$, where $d_2 > d_3$. In contrast to the focal points 35, 37, and 39, the surface of the material 31 ruptures due to photoalteration about this fourth focal point 41. From this process, $d_2$ is determined to be the minimum depth within the material 31 at which photoalteration can take place, using the selected operating pulse energy, without causing the surface of the material 31 to rupture.

By repeating this process for several different focal point separations, data points for creating the focal point depth curve 19 (shown in FIG. 3) are empirically determined. Knowing the minimum depth at which photoalterations may be madefort a given pulse energy, the combination of focal point depth, pulse energy, and focal point separation are optimized for separating a surface layer from a material, with the surface layer being relatively thin in comparison to the overall thickness of the material. Although the operating pulse energy of the pulsed laser beam is determined based on the pulse energy curve 17 prior to the process of empirically determining the data points for the focal point depth curve 19, the order of these processes may vary or may occur independent of one another.

EXAMPLE

Agarose Gel

The empirical processes described in connection with the curves 17 and 19 were conducted using agarose gel as the material. Agarose gel has physical properties that are similar to those of the human cornea. In this example, the gathered data points correspond to the data shown in the graph of FIG. 3. Focal point separations ranging from about 1 µm through about 10 µm at 1 µm intervals were used. At each focal point separation, a bubble pattern was produced from photoalteration of the agarose gel using a raster scan pattern, and the pulse energy for layer separation of the agarose gel without appreciable tearing was determined by examining the bubble patterns. For example, after identifying each of the corresponding data points for the pulse energy curve 17, a raster scan pattern was initiated in the agarose gel. This raster scan pattern included a decreasing sub-surface focal point depth within the gel along selected adjacent scan lines within the pattern. The focal point depths were decreased until gas breakthrough at the surface of the agarose gel was observed, and the immediately previous scan depth was recorded as the minimum focal point depth for the corresponding combination of focal point separation and pulse energy.

Figure 6:
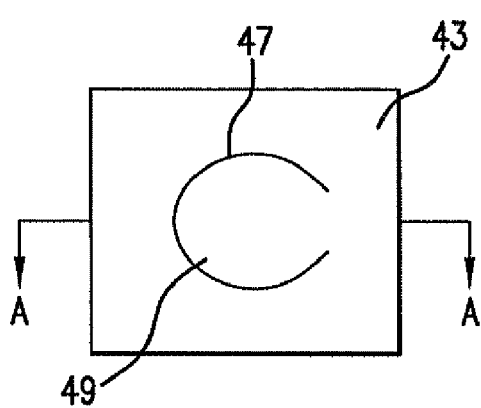
FIG. 6 is a top view of a surface layer formed in agarose gel by a pulsed laser beam in accordance with one embodiment.
Figure 7:
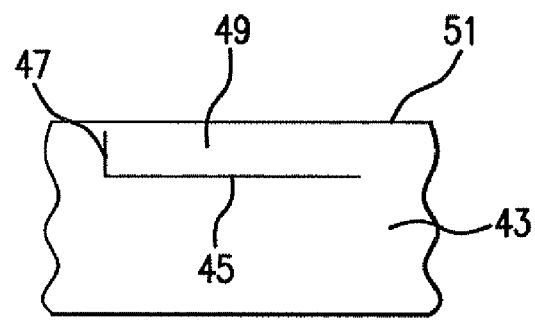
FIG. 7 is sectional view of the agarose gel shown in FIG. 6 along line A-A.

The minimum focal point depth and the separability of the surface layer of the agarose gel were then tested for each of the focal point separations. The data gathered from this test was used to generate the focal point depth curve 19. FIG. 6 is a top view of a surface layer 49 formed in the agarose gel 43 by a pulsed laser beam in accordance with one embodiment, and FIG. 7 is sectional view of the material 43 shown in FIG. 6 along line A-A. In this embodiment, a focal point pattern was used to create the separable surface layer 49 from the agarose gel 43. A first scan pattern was used to photoalter a bed 45 below a surface 51 of the agarose gel 43, then a second scan pattern was used to photoalter a periphery 47 such that the surface layer 49 could be lifted as a flap from the agarose gel 43. At focal point separations of about 3 μm and above, separability of the flap was confirmed. At focal point separations of about 1 μm and about 2 μm, the resulting flaps were too thin to be lifted. From this process, the optimum balance between pulse energy, minimum focal point depth, and focal point separation for the agarose gel 43 was found to be at a focal point separation of about 3 μm, a pulse energy of greater about 0.2 μJ, and a minimum focal point depth of about 12 μm.

The relationship of pulse energy and focal point separation may be pre-determined for multiple materials and stored for future use (e.g., when desiring to photoalter the applicable material). Similarly, the minimum focal point depth may be pre-determined for multiple materials, based on the corresponding selected pulse energy and/or focal point separation, and stored for photoaltering the appropriate material.

Thus, systems and methods of photoaltering a material are disclosed. In corneal tissue applications, the disclosed systems and methods are capable of producing relatively thin flaps (e.g., having a thinness of about 70 μm to about 90 μm or less). While embodiments of this invention have been shown and described, it will be apparent to those skilled in the art that many more modifications are possible without departing from the inventive concepts herein. The invention, therefore, is not to be restricted except in the spirit of the following claims.

What is claimed is:

1. A method of photoaltering tissue of a human eye in a scan region using a pulsed laser beam, the method comprising the steps of:
   selecting a first pulse energy and a focal point separation of successive pulses of the pulsed laser beam based on a relationship of pulse energy, and focal point separation combinations enabling layer separation of the tissue by photoalteration, the relationship having a slope and having a distinct change in the slope, the distinct change in the slope associated with a second pulse energy on the relationship, the first pulse energy being equal to or less than the second pulse energy;
   selecting a focal point depth using the first pulse energy and the focal point separation such that the pulsed laser beam does not cause a gas to rupture a surface of the tissue, the focal point depth being a sub-surface depth; and
   scanning the pulsed laser beam along the scan region at the first pulse energy, the focal point depth, and the focal point separation.

2. The method of claim 1, wherein the scanning step comprises scanning the pulsed laser beam with the operating focal point separation between about 1 μm and about 8 μm.

3. The method of claim 1, wherein the scan region underlies a surface layer of the tissue, and wherein the scanning step comprises at least partially separating the surface layer from the tissue.

4. The method of claim 1 further comprising, prior to the selecting step, determining the relationship based on a minimum pulse energy for layer separation of the tissue.

5. The method of claim 1, wherein the relationship has a first region and a second region adjacent to the first region, the first region associated with a first slope, the second region associated with a second slope, and wherein the method further comprises, prior to the step of selecting a first pulse energy and a focal point separation, comparing a difference between the first slope and the second slope with a pre-determined value to determine the distinct change in the slope.

6. The method of claim 1, wherein the scanning step comprises scanning the pulsed laser beam at a repetition rate between about 30 MHz and about 1 GHz.

7. The method of claim 1, wherein the scanning step comprises scanning the pulsed laser beam with the operating pulse energy at less than about 800 nanojoules.

8. A method of separating a surface layer from a tissue of a human eye via photoalteration by a pulsed laser beam, the method comprising:
   determining a relationship for the tissue based on laser pulse energies enabling layer separation of the tissue through photoalteration as a function of focal point separations of successive pulses of the pulsed laser beam within the tissue, the relationship having a slope;
   identifying a pulse energy value from the relationship corresponding to a distinct change of the slope;
   generating the pulsed laser beam, each pulse of the pulsed laser beam having an energy less than or equal to the pulse energy value; and
   scanning the pulsed laser beam along a region within the tissue with an operating focal point separation corresponding with the pulse energy value, the region underlying the surface layer, wherein scanning comprises minimizing a focal point depth of the pulsed laser beam such that the pulsed laser beam does not cause a gas to rupture a surface of the tissue, the focal point depth based on the pulse energy value and the operating focal point separation.

9. The method of claim 8, wherein the determining step comprises measuring a minimum pulse energy for layer separation in the tissue material at each of a plurality of laser pulse focal point separations.

10. The method of claim 8, wherein the determining step comprises measuring a sufficient pulse energy for a desired quality of layer paration in the tissue at each of a plurality of laser pulse focal point separations.

11. The method of claim 8, wherein the scanning step comprises scanning the beam of laser pulses along the region within the tissue material in a pattern providing substantially consistent focal point separations between the laser pulses.

12. A system for sub-surface photoalteration of a tissue of a human eye, the apparatus comprising:
   a laser configured to produce a pulsed laser beam having a first pulse energy, a sub-surface focal point depth, and a focal point separation of successive pulses of the pulsed laser beam; and
   a controller coupled to the laser, the controller configured to:
      determine the first pulse energy and the focal point separation based on a relationship of pulse energy and focal point separation combinations enabling layer separation of the tissue by photoalteration, the relationship having a slope and having a distinct change in the slope, the distinct change in the slope associated with a second pulse energy on the relationship, the first pulse energy being equal to or less than the second pulse energy; and
      determine the focal point depth at the first pulse energy and the focal point separation such that the pulsed laser beam at the focal point depth does not cause a gas to rupture a surface of the tissue.

13. The system of claim 12, wherein the pulsed laser beam has a pulse frequency selected from a range of about 30 MHz to about 1 GHz.

14. The system of claim 12, wherein the first pulse energy is less than or equal to about 800 nanojoules.

15. The system of claim 12, wherein the first focal point separation is between about 1 μm and about 8 μm.

16. The system of claim 12, wherein the laser is further configured to scan the pulsed laser beam along a scan region of the material to at least partially separate a surface layer from the tissue, the scan region underlying the surface layer of the tissue.

17. The system of claim 12, wherein the relationship is based on a minimum pulse energy for layer separation of the tissue by photoalteration.

* * * * *